United States Patent [19]

Sommer

[11] Patent Number: 4,562,148

[45] Date of Patent: Dec. 31, 1985

[54] ANALYTICAL ELEMENT AND METHOD FOR PREVENTING REAGENT MIGRATION

[75] Inventor: Ronald G. Sommer, Elkhart, Ind.

[73] Assignee: Miles Laboratories, Inc., Elkhart, Ind.

[21] Appl. No.: 318,755

[22] Filed: Nov. 6, 1981

[51] Int. Cl.$^4$ .................. G01N 33/54; C12Q 1/54
[52] U.S. Cl. .......................... 435/7; 422/56; 427/2; 436/518; 436/810; 435/14; 435/805
[58] Field of Search .................. 435/7, 4, 805, 810, 435/14, 25, 28; 422/55, 56, 57, 58, 61; 436/528, 529, 530, 518, 810; 427/2

[56] References Cited

U.S. PATENT DOCUMENTS

| | | | |
|---|---|---|---|
| 4,059,405 | 11/1977 | Sodickson et al. | 436/44 |
| 4,144,306 | 3/1979 | Figueras | 435/14 |
| 4,153,668 | 5/1979 | Hill et al. | 422/57 |
| 4,166,093 | 8/1979 | Smith-Lewis et al. | 435/14 |
| 4,168,146 | 9/1979 | Grubb et al. | 435/7 |
| 4,211,845 | 7/1980 | Genshaw et al. | 435/14 |
| 4,233,402 | 11/1980 | Maggio et al. | 435/7 |
| 4,235,601 | 11/1980 | Deutsch et al. | 422/56 |
| 4,238,565 | 12/1980 | Hornby et al. | 435/7 |
| 4,247,297 | 1/1981 | Berti et al. | 435/14 |
| 4,258,001 | 3/1981 | Pierce et al. | 435/7 |
| 4,273,868 | 6/1981 | Walter et al. | 435/14 |
| 4,279,992 | 7/1981 | Boguslaski et al. | 435/7 |
| 4,283,491 | 8/1981 | Dappen | 435/805 |
| 4,299,916 | 11/1981 | Litman et al. | 435/7 |
| 4,303,753 | 12/1981 | Lam | 435/805 |
| 4,336,330 | 6/1982 | Bauer | 435/14 |
| 4,361,648 | 11/1982 | Chen | 435/14 |
| 4,376,827 | 3/1983 | Stiso et al. | 422/56 |
| 4,385,114 | 5/1983 | Guthlein et al. | 435/28 |
| 4,390,343 | 6/1983 | Walter | 435/7 |

*Primary Examiner*—Esther M. Kepplinger
*Attorney, Agent, or Firm*—Roger N. Coe

[57] ABSTRACT

The invention provides an analytical element and a method for preparing an analytical element for evaluation of a liquid sample with respect to a particular analyte by (a) incorporating a carrier with a composition in a liquid, the composition comprising at least one reagent of an analyte-detecting system, under conditions effective to ionize a reagent migration inhibiting substance, which substance is insoluble in said liquid when in its nonionized form and soluble in said liquid when ionized, and drying the carrier; and then (b) incorporating the carrier of (a) with a second composition in a liquid different from that of (a), the composition comprising the remaining reagents of the analyte-detecting system which are reactive with the at least one reagent of (a) and a reagent migration inhibiting substance which is soluble in said liquid when in its nonionized form, which liquid is effective to prevent reaction of the second composition with the at least one reagent of (a) prior to contact of the element with the sample and to prevent the migration inhibiting substance from ionizing prior to contact with the sample, and drying the carrier. Preferably, conditions which ionize the reagent migration inhibiting substance are the use of an aqueous liquid at a pH of at least about 5. Preferably, the reagent migration inhibiting substance is a monoester maleic acid polymer such as a copolymer of methyl vinyl ether and the monomethylester of maleic acid. The liquid of (b) is preferably an organic liquid, such as acetone.

19 Claims, No Drawings

ANALYTICAL ELEMENT AND METHOD FOR PREVENTING REAGENT MIGRATION

BACKGROUND OF THE INVENTION

1. Field of the Invention

This invention relates to improvements in the field of test devices or elements for evaluation of a fluid sample, such as a biological liquid. In particular, this invention relates to devices or elements incorporated with assay reagents, including those for homogeneous specific binding assays.

2. Brief Description of the Prior Art

Test strips and similar solid state analytical elements have become commonplace in the analysis of various types of fluid samples, particularly biological liquids. They have been advantageous in, for example, the diagnosis of disease. They have been known and used for many years in a wide variety of fields, particularly as in vitro diagnostic devices for the detection of various urine and blood components such as glucose, protein, occult blood and so forth. For example, see U.S. Pat. Nos. 3,012,976; 3,164,534; and 3,485,587.

Test devices have been prepared which can be used to perform specific binding assays. Specific binding assays are useful for determining various organic substances of diagnostic, medical, environmental and industrial importance which appear in liquid mediums at very low concentrations. They are based on the specific interaction between the bindable analyte under determination, also referred to as a ligand, and a binding partner therefor. Where one of the analyte and its binding partner is a hapten or antigen and the other is a corresponding antibody, the assay is known as an immunoassay. For example, see U.S. Ser. Nos. 255,521 (now U.S. Pat. No. 4,447,527), 202,378 (filed Oct. 30, 1980, and now abandoned), and 253,147 (now U.S. Pat. No. 4,442,204), each of which discloses such a specific binding assay device and is commonly assigned herewith.

These test strips and similar devices have been compromised in the reliability of the results they provide when the application of sample has caused the migration of reagents away from the point of sample application to the device. This causes a nonuniformity of reagent concentrations throughout the device and resulting nonuniformity of detectable signal or response level. Because of this, a single device, which has been contacted with a single sample, can present an infinite variety of signal levels depending on which portion of the device surface is used to take a reading.

The approach which has hetertofore been used in attempts to avoid what has been referred to as a "ringing" effect has been the use of spreading layers. For example, see U.S. Pat. No. 3,992,158 and U.K. Patent Application GB No. 2,052,057. They assert that because spreading occurs in the spreading layer and the spread sample is presented to the reagent-containing layer without lateral hydrostatic pressure, the "ringing" phenomenon is avoided. These layers add complexity and expense to the manufacture of test devices.

SUMMARY OF THE INVENTION

The present invention addresses and solves the problem of reagent migration and also avoids the need for spreading layers. A uniform concentration of reagent throughout the device is maintained even after application of the liquid sample. Reliably uniform and accurate signal levels can be obtained without regard to which portion of the device surface is read and with devices substantially simpler than those requiring spreading layers.

The invention provides a method for preparing an analytical element useful for evaluation of a liquid sample with respect to a particular analyte. The method comprises (a) incorporating a carrier with a composition in a liquid, the composition comprising at least one reagent of an analyte-detecting system, under conditions effective to ionize a reagent migration inhibiting substance which substance is insoluble in said liquid when in its nonionized form and soluble in said liquid when ionized, and drying the carrier; and then (b) incorporating the carrier of (a) with a second composition in a liquid different from that of (a), the composition comprising the remaining reagents of the analyte-detecting system which are reactive with the at least one reagent of (a) and a reagent migration inhibiting substance which is soluble in said liquid when in its nonionized form, which liquid is effective to prevent reaction of the second composition with the at least one reagent of (a) prior to contact of the element with the sample and to prevent the migration inhibiting substance from ionizing prior to contact with the sample, and drying the carrier.

Preferably, the reagent migration inhibiting substance is a monoester maleic acid polymer, such as a copolymer of methylvinyl ether and the monomethylester of maleic acid, and the conditions which ionize the reagent migration inhibiting substance are that the liquid of (a) is aqueous and has a pH of at least about 5, preferably achieved by inclusion of a buffer. The liquid of (b) is preferably an organic liquid, such as acetone. The advantages achieved by the invention are especially valuable in specific binding assays, e.g., immunoassay elements. In this preferred embodiment, when an aqueous sample is added to a specific binding assay strip prepared according to the invention, the conjugate, described in detail below, is momentarily trapped in the water insoluble, nonionized acid form of the reagent migration inhibiting substance and prevented from migrating while the sample spreads. However, as soon as the buffer of step (a) has time to exert its ionizing effect the reagent migration inhibiting substance is converted to its ionic, soluble form, and the conjugate is freed to participate in the analyte-responsive reaction.

DESCRIPTION OF THE PREFERRED EMBODIMENTS

This invention provides test devices having all of the convenience features of conventional test strips and other analytical elements of similar design. The medium to be assayed can be a naturally occurring or artifically formed liquid suspected to contain the analyte, and usually is a biological fluid or a dilution thereof. Biological fluids that can be assayed include serum, plasma, urine, saliva, and aminotic and cerebrospinal fluids.

The assay element of the invention can incorporate reagent compositions, herein termed analyte-detecting systems such as those known for evaluating blood, plasma, serum and urine constituents (analytes). These often include an enzyme or substrate specific for the analyte and additional necessary reagents, including redox indicators and fluors, which undergo a detectable change. They can also include systems for the detection of an analyte (ligand) for which there is a specific binding partner and, conversely, systems for the detection of the capacity of a liquid medium to bind the analyte or ligand (usually due to the presence of a binding partner for it in the medium). The evaluation of a liquid sample with respect to a particular analyte is contemplated to include all of these assay approaches. The analyte is usually a peptide, polypeptide, protein, carbohydrate, glycoprotein, steroid, or other organic molecule for which a specific binding partner exists in biological systems or can be synthesized. Therapeutic drug monitoring is a valuable application of these specific binding assay elements.

The carrier used for analytical elements of this invention can take on many forms and is intended as being broad in context. It can comprise one or more appropriate materials or mediums of similar or different absorptive or other physical characteristics. For example, see U.S. Pat. Nos. 3,552,928; 4,046,514; and 4,845,247. Preferably the carrier comprises a bibulous material, such as filter paper, into which a solution or suspension of the reagents of the analyte-detecting system is impregnated. All of these carrier concepts can be employed in this invention, as can others. Whichever material is chosen for the carrier, whatever its composition or configuration, its selection will be dictated by the reagent system and the anticipated use of the device.

Devices having these assay systems provide a detectable response, primarily electromagnetic radiation signals such as fluorescence, phosphorescence, chemiluminescence, and a change in light absorption or reflectance in or outside the visible spectrum related to the presence or amount of the analyte (ligand) under assay in the liquid sample. The detectable response can be observed through the senses directly or by use of ancillary detection means, such as a spectrophotometer, ultraviolet light-sensing equipment, fluorometer or other sensing means.

PREPARATION OF THE TEST DEVICE

During the course of extensive studies to overcome the difficulties caused by reagent migration numerous compounds were evaluated. These compounds included Klucel ® LF and Klucel G hydroxypropyl cellulose (Hercules, Inc., Wilmington, DE), Gafquat 734 ® copolymer of quaternized dimethylaminoethyl methacrylate and vinylpyrrolidone (GAF Corp., New York, NY), Gantrez ® AN-139 copolymer of methylvinyl ether and maleic anhydride (GAF Corp., supra), cellulose acetate (Eastman Chemical Products, Inc., Kingsport, TN), and Natrosol ® MR and Natrosol LR hydroxyethylcellulose (Hercules, Inc., supra). None demonstrated an ability to solve the problem.

As in the case of conventional devices, the present invention provides a solid carrier of one sort or another incorporated with all of the reagents necessary to perform a given assay whereby the user has only the task of bringing the test device into contact with the sample to be tested and measuring the resulting response. Unlike such conventional devices, those of the present invention achieve the reagent migration inhibiting advantages as described and demonstrated, in detail, by the following description and examples.

As such, the present invention provides test devices which are substantially free of reagent migration upon being contacted with a liquid sample, with its undesirable affect on reliability of results. These test devices are provided by a method which comprises (a) incorporating a carrier with a composition in a liquid, the composition comprising at least one reagent of an analyte-detecting system, under conditions effective to ionize a reagent migration inhibiting substance which is insoluble in said liquid when in its nonionized form and soluble in said liquid when ionized, and drying the carrier; and then (b) incorporating the carrier of (a) with a second composition in a liquid different from that of (a), the composition comprising the remaining reagents of the analyte-detecting system which are reactive with the at least one reagent of (a) and a reagent migration inhibiting substance which is soluble in said liquid when in its nonionized form, which liquid is effective to prevent reaction of the composition of (b) with the at least one reagent of (a) prior to contact of the element with the sample and to prevent the migration inhibiting substance from ionizing prior to contact with the sample, and drying the carrier.

In one preferred embodiment the reagent migration inhibiting substance is a carboxylic acid polymer. Such carboxylic acid polymers can be, for example; copolymers of (1) methyl ether and the monomethylester of maleic acid, (2) methyl vinyl ether and the monoethylester of maleic acid, (3) methyl vinyl ether and a monopropylester of maleic acid, (4) methyl vinyl ether and a monobutylester of maleic acid, (5) vinyl acetate and the monomethylester of maleic acid (6) vinyl acetate and the monoethylester of maleic acid, (7) ethylene and the monomethyl ester of maleic acid, (8) ethylene and the monoethyl ester of maleic acid, (9) octadecyl vinyl ether and the monomethylester of maleic acid, and (10) octadecyl vinyl ether and the monomethyl ester of maleic acid.

The conditions effective to ionize the carboxylic acid polymer are, for example, achieved by use in step (a) of an aqueous liquid, the pH of which is at least about 5. This can be achieved, for example, by use of an appropriate buffers include sodium bicine [bicine is N,N-bis(2-hydroxyethyl)glycine], glycylglycine, AMP buffer [2-amino-2-methyl-1-propanol], TAPS [N-tris-(hydroxymethyl)-methyl-3-aminopropane sulfonic acid], and TRIS [tris-(hydroxymethyl)aminomethane].

In another embodiment the reagent migration inhibiting substance is a sulfonic acid polymer. For example, such sulfonic acid polymers can be polystyrene sulfonate, the copolymer of 2-acrylamido-2-methylpropanesulfonic acid and styrene, and polyvinyl sulfonic acid.

The conditions effective to ionize the polysulfonic acids are achieved, for example, by use in step (a) of an aqueous liquid, the pH of which is maintained in a range related to the pKa of the particular polysulfonic acid being used such that the sulfonic acid groups are ionized.

As contemplated in the present invention, solubility of the migration inhibiting substance does not require that complete solubilization occur. Solubilization of even a small percentage, such as ten percent, of the migration inhibiting substance present can be sufficient to achieve the desired result. The degree of solubilization which permits interaction between the components of the analyte-detecting system is all that is required.

The insolubility of the nonionized form of the migration inhibiting substance in the liquid of (a) must be such that the degree and rate of solubility is greatly decreased as compared to its ionized form.

As contemplated in the present invention, ionization of the migration inhibiting substances does not require that every or even most of the ionizable functionalities of the migration inhibiting substance be ionized. Indeed, with appropriate formulation of components in the device, an ionization of even a small percentage, such as ten percent, of the ionizable functionalities of the migration inhibiting substance can be sufficient to achieve the desired uniformity of reagent concentration and signal level throughout the device.

The reagent of (a) can comprise, for example, (i) a specific binding partner for the analyte or (ii) a specific binding partner for the analyte and a component which is reactive with a label conjugate, comprising a label component coupled to an analyte moiety or a specific binding analog thereof, to cleave the label component.

An embodiment of this is a method for preparing a homogeneous specific binding assay device for determining an analyte in a liquid sample, which method comprises (a) impregnating a carrier with a composition in an aqueous liquid, the composition comprising β-galactosidase, and antibody to the analyte, under conditions effective to ionize the carboxylic acid group of a monoester maleic acid polymer, and drying the carrier; and then (b) impregnating the carrier of (a) with a composition in an organic liquid, the composition comprising β-galactosyl-umbelliferone-analyte or analyte analog conjugate and a monoester maleic acid polymer, and drying the carrier.

One specific example is a method for preparing a homogeneous specific binding assay element for determining gentamicin in a liquid sample which method comprises (a) impregnating a carrier with a composition in an aqueous liquid, the composition comprising β-galactosidase and antibody to gentamicin, under conditions effective to ionize the carboxylic acid group of monoester maleic acid polymer, and drying the carrier; and then (b) impregnating the carrier of (a) with a composition in an acetone containing liquid, the composition comprising β-galactosyl-umbelliferone-sisomicin conjugate and a monoester maleic acid polymer, and drying the carrier.

Another embodiment is a method for preparing a homogeneous specific binding assay element for determining an analyte in a liquid sample which method comprises (a) impregnating the carrier with a composition in an aqueous liquid, the composition comprising glucose, peroxidase, glucose oxidase apoenzyme and antibody to the analyte, under conditions effective to ionize the carboxylic acid group of a monoester maleic acid polymer, and drying the carrier; and then (b) impregnating the carrier with a composition in an acetone-containing liquid, the composition comprising flavin adenine dinucleotideanalyte or analyte analog conjugate a tetraalkylbenzidine such as 3,3',5,5'-tetramethylbenzidine and a monoester maleic acid polymer, and drying the carrier.

Another embodiment is a method which, prior to (a) and (b), comprises the additional step of incorporating the carrier with an indicator reagent in a liquid effective to prevent reaction of the indicator reagent with the reagent of (a) prior to contact of the element with the sample and drying the carrier. Preferably this indicator reagent comprises a tetraalkylbenzidine such as 3,3',5,5'-tetramethylbenzidine.

One specific example of this embodiment is a method for preparing a homogeneous specific binding assay element for determining theophylline in a liquid sample which method comprises (1) impregnating a carrier with a composition in an acetone-containing liquid, the composition comprising 3,3',5,5'-tetramethylbenzidine, and drying the carrier; then (2) impregnating the carrier with a composition in an aqueous liquid, the composition comprising glucose, peroxidase, glucose oxidase apoenzyme and antibody to theophylline, under conditions effective to ionize the carboxylic acid group of a monoester maleic acid polymer, and drying the carrier; and then (3) impregnating the carrier with a composition in an acetone-containing liquid, the composition comprising flavin adenine dinucleotide-theophylline conjugate and a monoester maleic acid polymer, and drying the carrier.

Having experimented with a variety of concentrations of migration inhibiting substances it has been noted that the range of concentrations is not critical except that a sufficient minimum amount be included so as to achieve the desired effect. This minimum will be determined as compatible with the specific analyte-detecting system which is being used.

The device can be self-supporting or fixed to a support. The support can be opaque or transparent to light or other energy. A support of choice for any particular carrier will be compatible with the intended mode of signal detection. Supports include opaque supports and transparent support materials capable of transmitting electromagnetic radiation of a wavelength within the region between about 200 nanometers (nm) and about 900 nm. It may also be desirable to have a support that transmits one or more narrow wavelength bands and is opaque to adjacent wavelength bands. This could be accomplished, for example, by impregnating or coating the support with one or more colorants having suitable absorption characteristics. Typical supports are prepared from polystyrene, cardboard or a variety of other structurally stable materials.

EXPERIMENTAL EXAMPLES

The following Examples describe experiments performed in arriving at the present invention. While they illustrate the actual preparation and use of preferred embodiments, as well as providing comparisons supportive of the critical aspects of the invention, they do not limit the scope of the invention.

In Examples I–VI, fluorescence was measured using a fiber optic fluorometer specifically constructed (by Ames Company, Division of Miles Laboratories, Inc., Elkhart, IN) for measuring fluorescent emissions from analytical elements held in a horizontal position. The instrument used a continuous emission mercury lamp excitation light source, fiber optic read head, photomultiplier for fluorescence detection and a mechanical holder for the analytical element to be read. This mechanical element holder is similar to that of the Seralyzer ® reflectance photometer (Ames Company, supra). The element is held stationary in a horizontal position with the exposed surface which is to be read facing upwards and read from above. The fluorometer has wavelength interference filters to provide an excitation light source of 405 nanometers (nm) wavelength, which strikes the surface of the element at a 90° angle to the surface. The front face measurement of fluorescent light, emitted at a wavelength of 450 nm, is also made at a 90° angle to the surface of the pad.

EXAMPLE I

Element Prepared Without Polymer

This example reports experiments in which an element was prepared *without* a reagent migration inhibiting substance in accordance with the invention.

Element Preparation

In the preparation of the element, it is necessary to introduce a given amount of fluorescent conjugate β-galactose-umbelliferone-phenobarbital (β-GUPB.) into each element. The β-GUPB conjugate used in this example was prepared as described in example 9 of U.S. Pat. No. 4,279,992. Phenobarbital is useful as an anticonvulsant, hypnotic and sedative.

The solutions used in preparing the elements tested in these experiments contained the following components:

Aqueous solution

| Component | Quantity |
|---|---|
| (1) normal rabbit serum | 8 milliliters (ml) |
| (2) 1.2 Molar (M) sodium bicine and 0.1 M MgCl$_2$ in water, pH 9.0 | 20 ml |
| (3) βgalactosidase stock solution (165 Ames units/ml in 50 mM sodium bicine in water, pH 8.5) | 1 ml |
| (4) distilled water | 11 ml |

One Ames unit of β-galactosidase is the amount of enzyme which hydrolyses 1.0 micromole of orthonitrophenyl-β-D-galactopyranoside (ONPG) to orthonitrophenol per minute in an aqueous buffer, 0.05M sodium bicine, pH 8.5, containing 0.003M ONPG at 25° C.

Organic Solution

| Component | Quantity |
|---|---|
| (1) 4.8 micromolar (μM) β-GUPB in acetone | 10 ml |

A 3 inch by 6 inch piece of Whatman 31ET paper (Whatman, Inc. Clifton, NJ) was impregnated to saturation with the above prepared aqueous solution and dried in a convection oven at 50° centrigrade (C.) for 15 minutes. The organic solution was then impregnated to saturation into the paper containing the dried residue of the aqueous solution in the same way and the paper was again dried in a convection oven at 50° C. for 15 minutes.

This piece of impregnated paper was mounted onto the adhesive side of a silvered Mylar ® polyester film (3M Company, St. Paul, MN), forming a laminate which was further mounted on Y19 adhesive (3M Company, supra) having a release backing on one side. This final laminate was cut into one (1) centimeter (cm) wide ribbons which, after removal of the release backing, were mounted ¼ inch from the side edge of an 8.3 cm wide ribbon of Trycite ® polystyrene film (3M Company, supra). The Trycite-mounted laminate was transversely slit into 5 millimeter (mm) wide strips, each of the final strips therefore containing a 5 mm×10 mm segment of impregnated paper.

Analytical Procedure

Each device so-prepared was tested by contacting it with a 30 microliter (μl) aliquot of distilled water.

After positioning the device in the instrument strip holder, the aliquot of test solution was pipetted onto the exposed surface of the device and the strip holder was inserted into the fluorescence detection instrument.

The migration of the fluorescent species, after three (3) minutes of reaction of the conjugate with β-galactosidase, was measured by scanning the fluorescence emitted at different portions of the exposed surface area of the impregnated paper. A migration index, Rm, was calculated to be the ratio of the fluorescent signal in the center of the reagent pad (at the point of sample application) to the mean of the fluorescent signals at the front and back edges of each device.

Results

| Trial No. | Rm |
|---|---|
| 1 | 0.80 |
| 2 | 0.79 |
| 3 | 0.90 |
| mean = | 0.83 |
| standard deviation = | 0.06 |

Conclusion

The elements prepared as described in this example exhibited substantial variation in the fluorescence emitted at different portions of the exposed surface of the impregnated paper, as quantified by the migration index. This phenomenon causes a lack of reliability which is unacceptable.

EXAMPLE II

Polymer in First Impregnation Only (Aqueous)

This example reports experiments in which an element was prepared with a monoester maleic acid polymer included in the aqueous solution used for the first impregnation but not included in the second, organic, solution used for the second impregnation, by which the β-GUS conjugate was added.

Synthesis of the Monomethylester of Gantrez AN-139

Absolute methanol, 570 milliliters (ml) was placed in a one liter beaker, and 50 grams (g) of Gantrez AN-139 was added with rapid stirring on a magnetic stir plate. Concentrated sulfuric acid, 10 microliters (μl), was added and the slurry stirred at room temperature for one hour. The temperature was raised to 55°–60° Centigrade (C.) for three hours leaving the lid of the beaker slightly open. During this time, most of the solid material went into solution leaving a slightly hazy solution. This solution was cooled to room temperature and further stirred for 18 hours. None of the residual solids went into solution. The approximately 10% weight/weight (w/w) solution of the monomethylester of Gantrez AN-139 was stored at 4° C. and used as needed.

Elemental Preparation

In the preparation of the element it is necessary to introduce a given amount of fluorescent conjugate, β-galactose-umbelliferone-sisomicin (β-GUS), into each element. The β-GUS conjugate used in this example was prepared as described in example 1 of the U.S. Pat. No. 4,279,992. Sisomicin is a specific binding analog of gentamicin. Gentamicin is a water-soluble, broad spectrum aminoglycoside antibiotic. Antiserum to gentamicin was prepared as described in *Nature New Biol* 239:214(1972).

The solutions used in preparing the elements tested in these experiments contained the following components:

Aqueous solution

| Component | Quantity |
| --- | --- |
| (1) monomethylester of Gantrez AN-139 [10% weight/volume (w/v) in methanol] | 10 ml |
| (2) Sodium bicine buffer (50 mM, pH 8.5) | 90 ml |

Organic solution

| Component | Quantity |
| --- | --- |
| (1) acetone | 100 ml |
| (2) β-GUS stock solution [2250 μM in dimethylsulfoxide (DMSO)] | 0.20 ml |

Using the above aqueous solution a four inch wide roll of Whatman 31ET paper (Whatman, Inc., Clifton, NJ) was impregnated to saturation and dried for 7.5 minutes in a forced air Overly dryer (Overly Inc., Neenah, WI) at 50° C. The second dip (organic solution) was impregnated similarly. Thereafter the devices were prepared as described in Example I.

Analytical Procedure

The devices prepared as described in this example was tested using analytical procedures which were the same as those described in Example I except that the sample applied was 25 μl of a solution of β-galactosidase (2 units/ml) in 0.3M sodium bicine buffer, pH 8.5.

Results

| Trial No. | Rm |
| --- | --- |
| 1 | 0.66 |
| 2 | 0.78 |
| 3 | 0.77 |
| | mean = 0.71 |
| | standard deviation = 0.07 |

Conclusion

The elements prepared as described in this example exhibited substantial variation in the fluorescence emitted at different portions of the exposed surface of the impregnated paper, as quantified by the migration index. This phenomenon causes a lack of reliability which is unacceptable.

EXAMPLE III

Polymer in Both Impregnations

This example reports experiments in which a fluorescent element was prepared with a monoester maleic acid polymer included both in the aqueous solution used for the first impregnation and in the second, organic solution used for the second impregnation, by which β-GUPB conjugate was added.

Element Preparation

The solutions used in preparing the elements tested in these experiments contained the following components:

Aqueous solution

| Component | Quantity |
| --- | --- |
| (1) normal rabbit serum | 5 ml |
| (2) 2% (w/v) Gantrez ES-225 in 1.2 M sodium bicine and 0.1 M MgCl₂ in water pH 9.0 | 50 ml |
| (3) β-galactosidase stock solution (165 Ames units/ml of 0.05 M sodium bicine in water, pH 8.5) | 3.4 ml |
| (4) distilled water | 41.6 ml |

Gantrez ES-225 is the commercially available monoethylester Gantrez AN-119.

Organic solution

| Component | Quantity |
| --- | --- |
| (1) Gantrez ES-225 (50% (w/v) in ethanol) | 6 ml |
| (2) Acetone | 94 ml |
| (3) β-GUPB stock solution (948 μM in DMSO) | 0.50 ml |

Using the above solutions, the element preparation procedure thereafter was as described in Example II except that a 2 inch wide roll of Whatman 31ET paper was used, and the total drying time was five minutes.

Analytical Procedure

The devices prepared as described in this example were tested using analytical procedures which were the same as those described in Example I.

Results

| Trial No. | Rm |
| --- | --- |
| 1 | 0.98 |
| 2 | 0.94 |
| 3 | 0.96 |
| | mean = 0.96 |
| | standard deviation = 0.02 |

Conclusion

The elements prepared as described in this example exhibited negligible variation in the fluorescence emitted at different portions of the exposed surface of the impregnated paper, as quantified by the migration index. This demonstrates that the improvement in accordance with the invention overcomes the lack of reliability which plagued the prior art devices, as shown in Examples I and II, and also demonstrates that this improvement is not mitigated by including the migration inhibiting substance in both impregnations.

EXAMPLE IV

Polymer in Second Impregnation Only

This example reports experiments in which a substrate-labeled fluorescent immunoassay element was prepared with a monoester of maleic acid polymer included only in the second, organic solution used for impregnation of the β-GUPB conjugate. The polymer was not included in the aqueous solution used for the first impregnation.

Element Preparation

The solutions used in preparing the elements tested in these experiments contained the following components:

Aqueous solution

| Component | Quantity |
| --- | --- |
| (1) normal rabbit serum | 8 ml |
| (2) 1.2 M sodium bicine, 0.1 M MgCl$_2$ and 0.1% (w/v) sodium azide in water, pH 9.0 | 20 ml |
| (3) β-galactosidase stock solution (165 Ames units/ml in 50 mM sodium bicine buffer, pH 8.5) | 1 ml |
| (4) distilled water | 11 ml |

Organic solution

| Component | Quantity |
| --- | --- |
| (1) 4.8 μM β-GUPB and 3% (w/v) Gantrez ES-225 in acetone | 10 ml |

Using the above solutions, devices were prepared by the procedure described in Example I.

Analytical Procedure

The devices prepared as described in this example were tested using test solutions and analytical procedures which were the same as those described in Example I.

Results

| Trial No. | Rm |
| --- | --- |
| 1 | 0.96 |
| 2 | 0.97 |
| 3 | 0.98 |
| mean = | 0.97 |
| standard deviation = | 0.01 |

Conclusion

The elements prepared as described in this example exhibited negligible variation in the fluorescence emitted at different portions of the exposed surface of the impregnated paper, as quantified by the migration index. This demonstrates that the improvement in accordance with the invention overcomes the lack of reliability which plagued the prior art devices as shown in Examples I and II, as well as demonstrating that the migration inhibiting substance need only be included in the second impregnation.

EXAMPLE V

Alternate Polymer in Second Impregnation Only

Substrate labeled fluorescent Immunoassay Element for Phenobarbital

This example reports experiments in which a substrate labeled fluorescent immunoassay element was prepared with a monoester maleic acid polymer included only in the second, organic solution used for impregnation of the β-GUPB conjugate. The polymer was not included in the aqueous solution used for the first impregnation.

Element Preparation

The solutions used in preparing the elements tested in these experiments contained the following components.

Aqueous solution

| Component | Quantity |
| --- | --- |
| (1) 1.2 M sodium bicine and 0.1 M MgCl$_2$ in water, pH 9.0 | 7.5 ml |
| (2) antiserum to phenobarbitol | 6 ml |
| (3) β-galactosidase stock solution (176 Ames units/ml 50 mM sodium bicine in water, pH 8.5) | 0.5 ml |
| (4) water | 1.0 ml |

Organic solution

| Component | Quantity |
| --- | --- |
| (1) 1% (w/v) Gantrez BS-335-I (monoisopropylester of Gantrez AN-119) in acetone | 15 ml |
| (2) β-GUPB stock solution (958 μM in DMSO) | 0.188 ml |

Antiserum to phenobarbital was collected from rabbits which were immunized with a phenobarbital-bovine serum albumin immunogen conjugate. Using the above solutions, the element preparation procedure thereafter was as described in Example II except that a 2 inch wide roll of Whatman 31 ET paper was used.

Analytical Procedure

The devices prepared as described in this example were tested using analytical procedures which were the same as those described in Example I, except that the samples were 30 μl of an aqueous solution containing 5% (v/v) normal human serum and phenobarbital (3 μg/ml).

Results

| Trial No. | Rm |
| --- | --- |
| 1 | 1.04 |
| 2 | 0.98 |
| 3 | 0.99 |
| mean = | 1.00 |
| standard deviation = | 0.03 |

Conclusion

The elements prepared as described in this example exhibited negligible variation in the fluorescence emitted at different portions of the exposed surface of the impregnated paper, as quantified by the migration index. This demonstrates that the improvement in accordance with the invention overcomes the lack of reliability which plagued the prior art devices as shown in Examples I and II, as well as demonstrating the use of another migration inhibiting substance. Further, the experiments of this example demonstrate the compatability of the migration inhibiting substance with a complete substrate-labeled immunoassay system.

EXAMPLE VI

Substrate-Labeled Fluorescent Immunoassay Element for Gentamicin

This example reports experiments in which a substrate-labeled fluorescent immunoassay element for gentamicin was prepared with a monoester maleic acid polymer included only in the second, organic solution used for impregnation of the $\beta$-GUS conjugate. The polymer was not included in the aqueous solution used for the first impregnation.

Element Preparation

The solutions used in preparing the elements tested in these experiments contained the following components:

Aqueous solution

| Component | Quantity |
|---|---|
| (1) 1.2 M sodium bicine and 0.1 M MgCl$_2$ in water, pH 9.0 | 7.5 ml |
| (2) antisera to gentamicin | 1.2 ml |
| (3) $\beta$-galactosidase stock solution (160 Ames units/ml 50 mM sodium bicine in water, pH 8.5) | 0.5 ml |
| (4) water | 5.8 ml |

Organic solution

| Component | Quantity |
|---|---|
| (1) 2% (w/v) Gantrez ES-225 monoethylester in acetone | 15 ml |
| (2) 2.8 mM $\beta$-GUS stock solution (in 0.0005 M sodium formate, 0.1% (w/v) sodium azide, pH 3.5) | 25.7 $\mu$l |

Using the above solutions, devices were prepared by the procedure described in Example III.

Analytical Procedure

The devices prepared as described in this example were tested using test solutions and analytical procedures which were the same as those described in Example I except that the samples were 30 $\mu$l of an aqueous solution containing 10% normal human serum and gentamicin (4 $\mu$g/ml).

Results

| Trial No. | Rm |
|---|---|
| 1 | 0.95 |
| 2 | 0.94 |
| 3 | 0.95 |
| | mean = 0.95 |
| | standard deviation = 0.01 |

Conclusion

The improvement achieved in accordance with the invention is also demonstrated by this example in which a complete substrate-labeled fluorescent immunoassay system is incorporated into the analytical element.

Experiments using an organic dye, rather than the conjugates which were used in the previous examples have demonstrated the utility of the migration with the invention with a broad spectrum of reagent systems. This is shown by the following examples.

EXAMPLE VII

Bromophenol Blue Dye in the Second Dip with No Polymer in Either Dip

This example reports experiments in which strips containing a buffer and bromophenol blue dye were prepared where the first aqueous solution contained a buffer and the second organic solution contained bromophenol blue dye, a well known pH indicator, but neither solution contained a migration inhibiting substance in accordance with the invention.

Element Preparation

The solutions used in preparing the elements tested in these experiments contained the following components:

Aqueous Solution

| Component | Quantity |
|---|---|
| (1) 0.6 M sodium bicine and 0.05 M MgCl$_2$ in water, pH 9.0 | 10 ml |

Organic Solution

| Component | Quantity |
|---|---|
| (1) Bromophenol blue | 5.6 mg |
| (2) Acetone | 20 ml |

Using the above solutions the element preparation procedure thereafter was as described in Example II except that a 2 inch wide roll of Whatman 54 paper was used.

Analytical Procedure

Three strips were placed on a laboratory bench top and 20 $\mu$l of water was pipetted slowly onto the center of the impregnated paper while carefully observing the strip for color uniformity.

Results

On each of the three strips most of the bromophenol blue dye was washed away from the center of the impregnated paper toward the edges leaving diminished color in the center.

Conclusion

Visual examination alone was sufficient to observe the nonuniformity of color in the strips prepared as reported in this example.

EXAMPLE VIII

Bromophenol Blue Dye in the Second Dip with Polymer in the Second Dip only

This example reports experiments in which strips containing a buffer and bromophenol blue dye were prepared where the first aqueous solution contained a buffer and the second organic solution contained bromophenol blue dye and a monoester of maleic acid polymer.

Element Preparation

The solutions used in preparing the elements tested in these experiments contained the following components.

Aqueous Solution

| Component | Quantity |
|---|---|
| (1) 0.6 M sodium bicine and 0.05 M MgCl$_2$ in water, pH 9.0 | 10 ml |

Organic Solution

| Component | Quantity |
|---|---|
| (1) Bromophenol blue | 5.6 mg |
| (2) Gantrez ES-225 (50% w/v in ethanol) | 1.2 ml |
| (3) Acetone | 20 ml |

Using the above solutions the element preparation procedure thereafter was as described in Example II except that a 2 inch wide roll of Whatman 54 paper was used.

Analytical Procedure

The analytical procedure was the same as for Example VII.

Results

On each of the three strips little or none of the bromophenol blue dye was washed away from the center toward the edges, leaving an impregnated strip which was visually observed to have uniform color intensity throughout.

Conclusion

This examples demonstrates the improvement achieved in accordance with the invention with a significantly different type of reagent, i.e., bromphenol blue dye, in the impregnated strip.

Although it has been described with particularity, numerous changes in the details of the invention can be resorted to without departing from the scope of the invention.

What is claimed is:

1. A method for preparing an analytical element useful for evaluation of a liquid sample for the presence of an analyte, comprising the steps of
    incorporating a single analyte detection layer with an aqueous solution of at least one reagent of an analyte detecting system, and a buffer capable of providing a pH of at least 5,
    drying the single analyte detection layer, and
    incorporating the dried single analyte detection layer with a solution comprising a solvent, any reagent or reagents other than said at least one reagent contained in said analyte detecting system, and an unionized ionizable reagent migration inhibiting substance selected from the group consisting of carboxylic acid polymers and sulfonic acid polymers, wherein said solvent is one in which the substance is insoluble in its ionized state, but soluble in its unionized state.

2. The method of claim 1 wherein the reagent migration inhibiting substance is a carboxylic acid polymer.

3. The method of claim 2 wherein the carboxylic acid polymer is selected from the group consisting of copolymers of (1) methyl vinyl ether and the monomethylester of maleic acid, (2) methyl vinyl ether and the monoethylester of maleic acid, (3) methyl vinyl ether and the monopropylester of maleic acid, (4) methyl vinyl ether and a monobutylester of maleic acid, (5) vinyl acetate and the monomethylester of maleic acid, (6) vinyl acetate and the monoethylester of maleic acid, (7) ethylene and the monomethylester of maleic acid, (8) ethylene and the monoethylester of maleic acid, (9) octadecyl vinyl ether and the monomethylester of maleic acid, and (10) octadecylvinyl ether and the monoethylester of maleic acid.

4. The method of claim 1 wherein the reagent migration inhibiting substance is a sulfonic acid polymer.

5. The method of claim 1 wherein the sulfonic acid polymer is selected from the group consisting of polystyrene sulfonate, the copolymer of 2-acrylamido-2-methylpropanesulfonic acid and styrene, and polyvinylsulfonic acid.

6. The method of claims 4 or 5 wherein the conditions effective to ionize the sulfonic acid polymer are achieved by use of an aqueous liquid, the pH of which is maintained in a range related to the pKa of the particular sulfonic acid polymer being used such that the sulfonic acid groups are ionized.

7. The method of claim 1 wherein the solvent is an organc solvent.

8. The method of claim 1 wherein the solvent is selected from toluene, acetone, chloroform, n-propane, methylene chloride and ethylene dichloride.

9. The method of claim 1 wherein the reactive reagent comprises a specific binding partner for the analyte.

10. The method of claim 1 wherein the at least one reagent comprises a specific binding partner for the analyte and a component which is reactive with a label conjugate, comprising a label component coupled to an analyte moiety or a specific binding analog thereof, to cleave the label component.

11. The method of claim 1 which, prior to (a) and (b) comprises the additional step of incorporating the single analyte detection layer with an indicator reagent in a liquid effective to prevent reaction of the indicator reagent with the at least one reagent prior to contact of the element with the sample and drying the single analyte detection layer.

12. The method of claim 11 wherein the indicator reagent comprises a tetraalkylbenzidine.

13. A method for preparing an assay element for determining an analyte in a liquid sample which method comprises:
    impregnating a single analyte detection layer with an aqueous composition comprising β-galactosidase and antibody to the analyte, under conditions effective to ionize the carboxylic acid group of a nonionized, ionizable monoester maleic acid polymer, and drying the single analyte detection layer; and then
    impregnating the dried carrier with a composition in an organic liquid, the composition comprising β-galactosyl-umbelliferone-analyte or analyte analog conjugate and a nonionized ionizable monoester maleic acid polymer, and drying the single analyte detection layer.

14. A method for preparing an assay element for determining gentamicin in a liquid sample which method comprises:
  impregnating a single analyte detection layer with an aqueous composition comprising β-galactosidase and antibody to gentamicin, under conditions effective to ionize the carboxylic acid group of a nonionized, ionizable monoester maleic acid polymer, and drying the single analyte detection layer; and then
  impregnating the dried single analyte detection with a composition in an acetone containing liquid, the composition comprising β-galactosyl-umbelliferonesisomicin conjugate and a nonionized, ionizable monoester maleic acid polymer, and drying the single analyte detection layer.

15. A method for preparing assay element for determining theophylline in a liquid sample which method comprises:
  impregnating a single analyte detection layer with a composition in an acetone-containing liquid, the composition comprising 3,3',5,5'-tetramethylbenzidine, and drying the single analyte detection layer; then
  impregnating the single analyte detection layer with a composition in an aqueous liquid, the composition comprising glucose, peroxidase, glucose oxidase apoenzyme and antibody to theophylline, under conditions effective to ionize the carboxylic acid group of a nonionized, ionizable monoester maleic acid polymer, and drying the single analyte detection layer; and then
  impregnating the single analyte detection layer with a composition in an acetone-containing liquid, the composition comprising flavin adenine dinucleotide-theophylline conjugate and a nonionized, ionizable monoester maleic acid polymer, and drying the single analyte detection layer.

16. A method for preparing an assay element for determining an analyte in a liquid sample which method comprises:
  impregnating the single analyte detection layer with a composition in an aqueous liquid, the composition comprising glucose, peroxidase, glucose oxidase apoenzyme and antibody to the analyte, under conditions effective to ionize the carboxylic acid group of a nonionized, ionizable monester maleic acid polymer, and drying the single analyte detection layer; and then
  impregnating the single analyte detection layer with a composition in an acetone-containing liquid, the composition comprising flavin adenine dinucleotide-analyte or analyte analog conjugate, 3,3',5,5'-tetramethylbenzidine and a nonionized, ionizable monoester maleic acid polymer, and drying the single analyte detection layer.

17. A test device for evaluation of a liquid sample for the presence of an analyte which comprises a single analyte detection layer incorporated with an analyte detecting system, buffer capable of providing a pH of at least 5, and a nonionized, ionizable reagent migration inhibiting substance selected from the group consisting of carboxylic acid polymers and sulfonic acid polymers.

18. The test device of claim 17 in which the reagent migration inhibiting substance is a copolymer of methyl vinyl ether and the monomethylester of maleic acid, methyl vinyl ether and the monoethylester of maleic acid, methyl vinyl ether and the monopropylester of maleic acid, methyl vinyl ether and a monobutylester of maleic acid, vinyl acetate and the monomethylester of maleic acid, vinyl acetate and the monoethylester of maleic acid, ethylene and the monomethylester of maleic acid, ethylene and the monoethylester of maleic acid, octadecyl vinyl ether and the monomethylester of maleic acid, or octadecylvinyl ether and the monoethylester of maleic acid, or mixtures thereof.

19. The test device of claim 17 in which the reagent migration inhibiting substance is polystyrene sulfonate, a copolymer of 2-acrylamido-2-methylpropanesulfonic acid and styrene, polyvinylsulfonic acid, or mixtures thereof.

* * * * *

UNITED STATES PATENT AND TRADEMARK OFFICE
CERTIFICATE OF CORRECTION

PATENT NO. : 4,562,148
DATED : December 31, 1985
INVENTOR(S) : Ronald G. Sommer

It is certified that error appears in the above-identified patent and that said Letters Patent are hereby corrected as shown below:

Col. 15, line 51, after the term "analyte" insert --whereby a single analyte detection layer is incorporated with an analyte detecting system comprising the steps of".

Col. 16, line 32, after the term "from" insert --the group consisting of".

Col. 16, line 63, delete the term "carrier".

Col. 16, line 63, after the term "dried" insert --single analyte detection layer".

Col. 17, line 11, after the term "detection" insert --layer--.

Col. 17, line 17, after the term "preparing" insert --an--.

Signed and Sealed this

Fifth Day of August 1986

[SEAL]

Attest:

DONALD J. QUIGG

Attesting Officer     Commissioner of Patents and Trademarks